United States Patent [19]

Denton, Jr.

[11] Patent Number: 4,781,940

[45] Date of Patent: Nov. 1, 1988

[54] METHOD FOR PRODUCING FILLER FOR MICROFILLED DENTAL COMPOSITE MATERIAL

[75] Inventor: Robert K. Denton, Jr., Allentown, N.J.

[73] Assignee: Johnson & Johnson Consumer Products, Inc., New Brunswick, N.J.

[21] Appl. No.: 66,445

[22] Filed: Jun. 26, 1987

[51] Int. Cl.$^4$ .......................... C08K 3/36; C08K 9/04; C08F 2/28

[52] U.S. Cl. ........................................ 427/2; 427/221; 428/404; 523/116; 524/853

[58] Field of Search ..................... 523/116; 427/2, 221; 428/404; 524/853

[56] References Cited

U.S. PATENT DOCUMENTS

| | | | |
|---|---|---|---|
| 3,862,920 | 1/1975 | Foster et al. | 523/116 |
| 4,180,913 | 1/1980 | Takeuchi et al. | 523/116 |
| 4,267,097 | 5/1981 | Michl et al. | 524/786 |
| 4,407,984 | 10/1983 | Ratcliffe et al. | 523/116 |
| 4,410,625 | 10/1983 | Koblitz et al. | 523/116 |
| 4,427,799 | 1/1984 | Orlowski et al. | 523/116 |
| 4,442,240 | 4/1984 | Suh | 523/202 |
| 4,617,327 | 10/1986 | Podszon | 523/116 |
| 4,674,980 | 6/1987 | Ibsen et al. | 523/116 |
| 4,696,955 | 9/1987 | Kuhlmann | 523/116 |
| 4,707,504 | 11/1987 | Walkowiak et al. | 523/116 |

*Primary Examiner*—Herbert J. Lilling
*Attorney, Agent, or Firm*—Charles J. Metz

[57] ABSTRACT

A filler for use in dental composites is made by the following process:

(a) finely divided silica, such as fumed silica, is coated with a polymerizable monomeric material by (e.g., an acrylic monomer) by mixing the silica with an organic solvent solution of the monomer;

(b) the solvent is removed by evaporation by any convenient means;

(c) the coated silica particles are individualized, as by screening, to produce a powder of a predetermined particle size (e.g., 90 microns or smaller); and (d) the resin is then polymerized.

Some individualization of the product of step (d) may be required. Light screening is usually sufficient.

3 Claims, No Drawings

METHOD FOR PRODUCING FILLER FOR MICROFILLED DENTAL COMPOSITE MATERIAL

The invention relates to an improved method for producing the cured resinous filler used in a microfilled dental composite material, to the filler produced thereby, and to the dental composite material utilizing the same.

BACKGROUND OF THE INVENTION

Microfilled dental composites are resinous materials, usually polymerizable acrylic materials, which contain a finely divided cured resin as a filler. Microfilled dental composites are used principally for asthetic reasons; cured microfilled composites can be polished to have a very pleasing and natural-appearing surface finish.

The conventional processes for producing microfill fillers are the following:

A resin, usually an acrylic resin, containing finely divided silica is polymerized in bulk. The polymerized material is then pulverized to a very fine particle size material by first hammer milling, followed by ball milling. This technique is both time and labor intensive, with the potential for high waste, because of the relatively inefficient milling steps that are required. Also, the process is limited to the use of resins that can be milled.

A second conventional process is polymerization from a solution of monomer in a suitable organic solvent that is a non-solvent for the polymer. The polymer (a "bead polymer") thereby precipitates from solution as it is formed. This is rather an expensive process, and it is difficult to use this process for producing a microfill filler containing an inorganic component such as colloidal silica.

This invention provides a process for making a microfill filler for use in dental composites that is easy to carry out, provides excellent control over the product, reduces waste (because there is no grinding step which usually entails some loss of material), and produces a microfill filler that can be used to make dental composite materials that, when cured, can possess a wide range of properties because the choice of which resins to use is not limited to those that can be milled.

BRIEF SUMMARY OF THE INVENTION

The process of the invention comprises the following steps:

(a) finely divided silica, such as fumed silica, is coated with a polymerizable monomeric material by mixing the silica with an organic solvent solution of the monomer;

(b) the solvent is removed by evaporation by any convenient means;

(c) the coated silica particles are individualized, as by screening, to produce a powder of a predetermined particle size (e. g., 90 microns or smaller); and (d) the resin is then polymerized.

Some individualization of the product of step (d) may be required. Light screening is usually sufficient.

THE PRIOR ART

U.S. Pat. No. 3,862,920 to Foster et al. discloses a composite dental filling material comprising a mixture of a finely divided, inert inorganic filler and the reaction product of an organic aliphatic diisocyanate and a hydroxylalkyl acrylate or methacrylate. The filler material can also contain at least one other ethylenically unsaturated monomer having at least two terminal acrylate groups.

In the paragraph bridging, columns 3 and 4, the filler is coated by dissolving a $\gamma$-methacryl-oxypropyl-trimethoxy-silane in a 30/70 water/acetone mixture; the acetone water is removed at 100° C.; the silane is condensed on the filler surface at 125° C.; and the coated filler is sieved through a 60$\mu$ silk. A similar disclosure is found in Orlowski et al U.S. Pat. No. 4,427,799.

U.S. Pat. No. 4,407,984 to Ratcliffe et al. discloses a dental composition comprising a liquid ethylenically unsaturated polymerizable material and a mixture of fine particle size fillers. In incorporating the filler, a diluent can be used (col. 4, lines 17 to 20), and the diluent is evaporated off prior to curing (col. 6, lines 52 to 57).

U.S. Pat. No. 4,089,763 to Dart et al. discloses a composition for repairing teeth where a polymerizable prepolymer is mixed with a filler using a diluent, which is removed by evaporation (col. 12, lines 3 to 21).

U.S. Pat. No. 3,868,447 to Kliment discloses a paste made of an organic solvent soluble hydrophilic copolymer of a hydroxy lower alkyl acrylate or methacrylate and of a diester of a glycol and acrylic or methacrylic acid, an active inorganic filler, e.g. silica and an organic solvent for the copolymer.

U.S. Pat. No. 4,180,913 to Takeuchi et al. discloses a filler for an $\alpha$-cyanoacrylate dental material which is prepared by mixing an $\alpha$-cyanoacrylate with the filler; and where a solvent is used (Example 2), it is removed by heat under reduced pressure.

DETAILED DESCRIPTION OF THE INVENTION

In the first step of the process of the invention, colloidal silica is coated with a polymerizable monomer. The silica is a known type of material. It usually has a particle size of less than about 1 micron. Fumed silica or other type of colloidal silica such as pyrogenic or precipitated silica can be used. The monomer used will ordinarily be an acrylic monomer such as triethylene glycol dimethacrylate, diethylene glycol dimethacrylate, other polyalkylene glycol acrylate or methacrylate, alkane diol diacrylate or dimethacrylate such as 1,6-hexamethylene glycol dimethacrylate or 1,10-decamethylene diol dimethacrylate, ethoxylated bisphenol-A dimethacrylate, or other similar material. The polymerizable monomer can be used alone or in mixtures thereof.

The colloidal silica is coated with the polymerizable monomer by mixing the silica (which may be first treated with a conventional silane coupling agent) with an organic solvent solution of the monomer, along with any polymerization catalysts that may be used. As a general rule, the solution will also contain a polymerization catalyst for the monomer, such as a peroxide, e. g., benzoyl peroxide, that will not be activated until a predetermined elevated temperature is attained. The catalyst is used in a catalytically effective quantity, e.g., from about 0.1 to about 3 weight percent, based on weight of monomer(s). The organic solvent selected will be one that can readily and conveniently be removed by evaporation at temperatures safely below the activation temperature of the catalyst. Useful solvents include haloalkanes such as methylene chloride and chloroform, ketones such as acetone or methyl ethyl ketone, dimethyl sulfoxide, alcohols, and other similar solvents that have the requisite dissolving power for the monomer and which can readily be evaporated completely at a temperature safely below the activation temperature of the catalyst. The specific solvent selected is not critical.

The proportion of silica to monomer is not narrowly critical. For instance, it can be varied from about 60 to about 85 weight percent silica, based on weight of silica and monomer. The proportion of monomer in the solvent solution has also not been found to be narrowly critical. For instance, it can vary from about 15 to about 40 weight percent monomer, based on weight of monomer plus solvent.

After preparing a slurry of silica in the monomer/solvent solution, the solvent is evaporated by any convenient means. The slurry can be placed in a tray and subjected to modest heating at atmospheric pressure, preferably in a forced air oven. Temperatures from just above room temperature up to about 50° C. can be used when the catalyst is benzoyl peroxide, whose activation temperature is about 90° C. After evaporation of all the solvent, the resulting material (which is colloidal silica coated with the monomer/catalyst mixture) is then individualized to form a powder containing particles of the desired size. Simple screening through an appropriately sized sieve can be used, if desired. For instance, to produce a powder containing particles having sizes of 90 microns or less, a 165 mesh screen (American Standard Sieve series) may be used.

After the screening, the monomer is then polymerized, as by heating to a temperature above the activation temperature of the peroxide catalyst. When using benzoyl peroxide, a temperature of about 120° C. is sufficient. The heating is preferably carried out under an inert atmosphere (as, for example, under nitrogen or under a vacuum) so as to avoid oxygen inhibition of the polymerization. A polymerization time of from about 4 to about 24 hours is usually sufficient. The heating is continued for a period of time sufficient to effect the polymerization of the monomer and to completely destroy all of the peroxide catalyst so that the coated silica will not have a deleterious effect on the stability of the dental composite material in which it is used as a filler. After the polymerization/heating step, the product is preferably again passed through the sieve to break up any agglomerates that might have formed. A major advantage of this invention is that no grinding or pulverizing step is needed.

The polymer-coated silica product of the invention is used as a filler in a microfilled dental composite material. The coated silica may be the only filler used, or it may be used in combination with other fillers such as conventional colloidal silica. The filler of the invention may be used in a two package system, using a peroxide catalyst, or it may be used in a light cured system using a photoinitiator catalyst system. Current practice favors light cured systems.

The resinous composite formulations in which the filler of the invention may be used include acrylic or methacrylic ester systems containing monomers such as bis-GMA, alkoxylated bisphenol-A dimethacrylate, alkane diol acrylates or methacrylates such as those enumerated above for use in making the filler of the invention, as well as polyalkylene glycol diacrylates and methacrylates such as those mentioned above. In the usual case, the filler of the invention will be used in proportions of from about 45 to about 55 weight percent, based on weight of filler of the invention plus monomer(s). As was indicated above, additional fillers may be used if desired. Such additional fillers include colloidal silica, barium glass, titanium dioxide, and other known fillers.

In the currently preferred light cured formulations, conventional photo-activator catalyst systems maybe used. These include combinations of alpha,beta-diketones and tertiary amines such as camphoroquinone and/or benzil plus N,N-dimethylaminoethyl methacrylate or ethyl 4-(N,N-dimethylamino)benzoate. If a two-package peroxide cured system is used, the catalyst system may be benzoyl peroxide and N,N-di-(2-hydroxyethyl)-p-toluidine. Other initiator systems may be used, if desired. The catalyst or initiator system is used in conventional catalytically effective proportions.

The example below illustrates the invention.

EXAMPLE 1

One hundred grams of OX-50 silica (a spherical precipitated silica having a particle size of about 0.04 micron) that had been treated with 5%, by weight, of A-174 silane (A-174 is gamma-methacryloxypropyltrimethoxysilane) is placed in a mixing vessel with a solution containing 120 grams of methylene chloride and 25 grams of the following monomer mixture:

70 parts by weight of a 9:1 (by weight) mixture of bis-GMA and bisphenol-A dimethacrylate;

30 parts by weight of triethylene glycol dimethacrylate; and 2 parts by weight of benzoyl peroxide.

The slurry is poured into a tray and the methylene chloride is evaporated by allowing the tray and its contents to stand in air at ambient temperature (about 23° C.) for 16 hours (overnight).

After evaporating the methylene chloride solvent, the coated silica is then passed through a 165 mesh screen. The sieved material is heated to 120° C. for 4 hours in a vacuum oven under a vacuum of 30 mm Hg (absolute pressure).

After the heating step, the powder is cooled, sieved again through a 165 mesh screen, and is then used as a filler in a dental composite material having the following formulation:

a. Cab-O-Sil M-5 silica (0.01 micron Pyrogenic silica), treated with 15% A-174 silane (by weight)—3.1 grams b. Filler of this invention—52.0 grams c. OX-50 Silica, treated with 5% A-174 silane—10.8 grams d. Light curing resin—the monomers are the same as those used to coat the silica filler, and the catalyst is 0.28% camphoroquinone, 0.12% benzil, and 1.2% ethyl 4-(N,N-dimethylamino)benzoate, the percentages of the catalyst system being based on weight of the resin—34.1 grams Cured samples of the above formulation were made by exposing the mixture to light from a commercial dental photoinitiator light source (Kulzer "Translux") for 60 seconds. Representative properties of the cured material are displayed below in Table I, compared with the same properties of cured samples of the current leading commercial microfilled dental composite material:

TABLE I

| | Example 1 | Commercial Control | Test Procedure |
|---|---|---|---|
| Filler Content (%) (Ashed Solids) | 55.6 | 51.8 | ASTM D-1579 |

TABLE I-continued

| | Example 1 | Commercial Control | Test Procedure |
|---|---|---|---|
| Rockwell 15T Hardness | 83.5 | 79.5 | ASTM D-617 |
| Transverse Strength, MPa | 73.4 | 65.0 | ASTM D-1184 |
| Flexural Modulus, MPa | 7000 | 5500 | ASTM D-790 |
| Compression Strength, MPa | 450 | 280 | ASTM D-695 |
| Diametral Tensile Strength, MPa | 50.5 | 40.0 | ADA Spec. 27 |
| Water Sorption, Mg/cm2 | 1.3 | 1.1 | ADA Spec. 27 |
| Linear Thermal Coefficient of Expansion, ppm | 36.1 | 63.6 | ASTM E-228 |

What is claimed is:

1. A process for the production of a filler for use in a microfilled dental composite formulation, which process comprises the steps of:
   (a) coating colloidal silica with a polymerizable monomer by mixing said silica with an organic solvent solution of said monomer and an effective amount of a polymerization catalyst, and then evaporating said solvent;
   (b) individualizing the coated silica by screening to product particles having a maximum size of about 90 microns;
   (c) polymerizing said monomer; and
   (d) individualizing the coated silica particles comprising the product of step (c) by screening.

2. The process of claim 1 wherein the monomer is an acrylic monomer.

3. The process of claim 2 wherein the acrylic monomer contains a peroxide catalyst, and wherein step (c) is carried out by heating the product of step (b) to a temperature above the activation temperature of said catalyst.

* * * * *